March 23, 1948. R. S. ROGERS Plant Pat. 794
APPLE TREE
Filed March 20, 1947
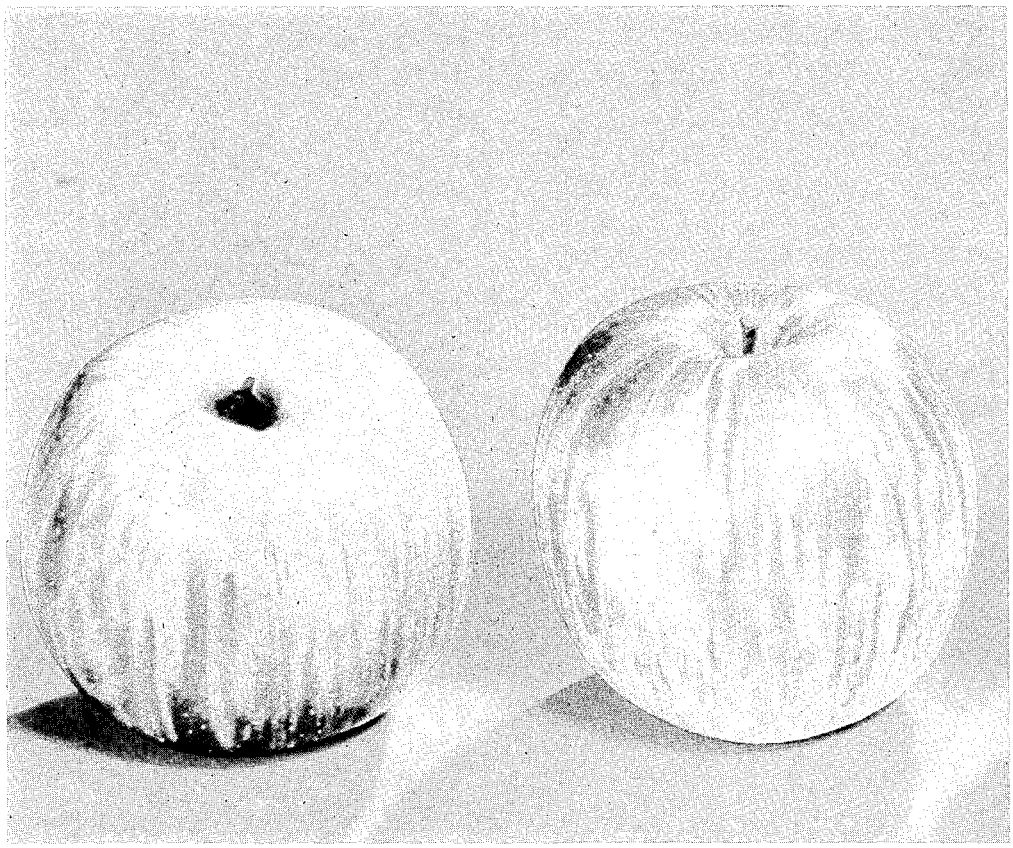
Inventor
R. S. Rogers, Deceased
by Everett R. Bridges
Administrator
By Robb & Robb
Attorneys Patented Mar. 23, 1948

UNITED STATES PATENT OFFICE

794

APPLE TREE

Rowland Sigel Rogers, deceased, late of Bloomfield, Ind., by Everett R. Bridges, administrator, Bloomfield, Ind., assignor to Stark Bro's Nurseries and Orchards Company, Louisiana, Mo., a corporation of Missouri Application March 20, 1947, Serial No. 735,848

1 Claim. (Cl. 47—62)

This invention relates to a new and distinct variety of apple tree, originating as a seedling and having a number of characteristics of commercial importance as regards habits of the tree and features of the fruit.

The fruit of this new variety resembles that of the well known Jonathan apple in respect to flavor, though less acid, and the Grimes Golden apple as to shape, but otherwise it is clearly distinguished therefrom. In reference to the color of the fruit, this new apple is bright red over a yellow ground color, the coloring appearing in stripes or streaks covering the exposed side of the fruit with solid red color imparting to it a very distinctive appearance. It is, furthermore, a high quality dessert apple, superior in eating quality to any other variety ripening at the corresponding period of this variety.

This new apple variety is also outstanding in its heavy bearing habit, producing big crops regularly every year, even under adverse climatic conditions.

A further important characteristic is that the new variety ripens at least three to four weeks ahead of Grimes Golden or Jonathan.

Asexual reproduction shows that these characteristics hold true through succeeding propagations.

In the drawing are shown obverse views of a specimen of this new apple depicting more particularly the striped or streaked side and the yellow base which imparts distinctiveness to the fruit.

The following is a detailed description of the new variety, giving color designations according to the conventional dictionary definition of terminology as well as corresponding color terms according to Ridgway's Color Standard:

Dates first and last picking: August 1st–August 10th.

*Tree*

Large; vigorous; upright; dense; open; rapid growing; hardy; very productive; regular bearer.

Trunk: Medium stocky; medium smooth.

Branches: Medium thick; smooth; much branching; Greyish Olive (Ridgway), Plate XLVI, Color 21''''. *Lenticels*—medium number; large.

Leaves: Length, 4½ inches; width, 2¼ inches. Large; wide; long; oval; taper-pointed; thick; dark green (Ridgway, Forest Green, Plate XVII, Color 29', tone M); rugose.

*Margin.*—Coarsely serrate.

*Petiole.*—Length, 1⅜ inches; medium length; medium thick.

Flowers: Dates of first and full bloom, March 31st–April 8th. Same date as Jonathan; medium size; pink.

*Fruit*

Maturity when described—eating stage.

Size: Uniform. Axial diameter, 3 inches; transverse, 2⅝ inches.

Shape: Oblong.

Cavity: Symmetrical; flaring toward apex; acute; even.

*Depth.*—¾ inch.

*Breadth.*—1⅛ inches.

Basin: Symmetrical; abrupt; even; pubescent.

*Depth.*—¼ inch.

*Breadth.*—1 inch.

Stem: Clubbed; medium slender; pubescent.

*Length.*—⅞ inch.

*Breadth.*—$\frac{1}{10}$ inch.

*Color.*—Verona Brown (Ridgway), Plate XXIX, Color 13'', tone K.

Calyx: Closed; persistent; broadly obtuse; length, ¼ inch; approximate at base; ascending; converged from base toward center.

*Outer surface.*—Pubescent.

*Inner surface.*—Pubescent.

Eye: Medium size; partially closed.

Skin: Thin; tough; smooth; glossy.

*Dots.*—Obscure; few; small; even; areolar. Color of dots—white. Distribution of dots—scattered over entire surface.

*Ground color.*—Apricot Yellow (Ridgway), Plate IV, Color 19, tone B. Color markings—striped; blushed. Color of markings—Scarlet Red (Ridgway), Plate I, Color 3. Bloom—wanting. Scarfskin—wanting. General color effect—bright red stripes on yellow ground presenting solid red color on exposed side of fruit.

Flesh: Juicy.

*Color of flesh.*—Satiny with yellowish greenish tint.

*Texture.*—Firm; tender; fine; crisp.

*Flavor.*—Subacid; rich.

*Aroma.*—Distinct.

*Quality.*—Best.

Core: Median.

*Bundle area.*—Medium size; broadly ovate; symmetrical; unsymmetrical at base; alternate.

*Halves of area.*—Equal.

*Bundles.*—Green; inconspicuous in two whorls.

*Alternate bundle.*—Approximate to calyx, reaches tube above stamens.

*Core lines.*—Meeting; in cross section indistinct; carpellary area—distinct; small.
*Calyx tube.*—Pubescent toward base; apex cone-shaped.
*Styles.*—Present at base; united toward base; pubescent toward base.
*Stamens.*—In one whorl; median.
*Axillary cavity.*—Wanting.
*Seed cells.*—Axile. Cell walls—thin; tough. Length, ½ inch; breadth, ¼ inch.
*Longitudinal section.*—Oval. Surface—entire smooth. Cross section—broad.

Seed:
*Number perfect.*—8; imperfect, 2.
*Number in one cell.*—2; length, ⅓ inch; breadth, ⅕ inch.
*Form.*—Obtuse.
*Color.*—Seal Brown (Ridgway), Plate XXXIX, Color 5''', tone M.

Use: Dessert; culinary.
Keeping quality: Medium.
Resistance to:
*Insects.*—Medium.
*Diseases.*—Good.

It is claimed:

A new and distinct variety of apple tree, characterized as to novelty by the bright red striped or streaked coloring of the fruit over yellow ground color; outstanding heavy bearing habit of the tree, producing big crops regularly every year; its earlier ripening period relative to Grimes Golden and Jonathan varieties; and the superior eating quality of the fruit, substantially as shown and described.

EVERETT R. BRIDGES.
*Administrator of the Estate of Rowland Sigel Rogers, Deceased.*